United States Patent [19]
Stimpson

[11] Patent Number: 5,114,555
[45] Date of Patent: May 19, 1992

[54] CONTINUOUS ISOELECTRIC SEPARATION

[75] Inventor: Donald I. Stimpson, Zion, Ill.

[73] Assignee: Monsanto Company, St. Louis, Mo.

[21] Appl. No.: 273,780

[22] Filed: Nov. 23, 1988

Related U.S. Application Data

[63] Continuation-in-part of Ser. No. 140,855, Jan. 5, 1988, abandoned.

[51] Int. Cl.$^5$ .................. G01N 27/26; B01D 57/02
[52] U.S. Cl. .................. 204/183.2; 204/301; 204/182.3; 204/182.6; 204/180.1
[58] Field of Search .................. 204/183.2, 301, 180.1, 204/301, 182.8, 182.9, 186.6, 182.3, 130, 131

[56] References Cited

U.S. PATENT DOCUMENTS

| | | | |
|---|---|---|---|
| 2,976,576 | 3/1961 | Wichterle et al. | 18/58 |
| 3,051,640 | 8/1962 | Treaxler | 204/182.6 |
| 3,240,692 | 3/1966 | Donnelly | 204/182.3 |
| 3,704,223 | 11/1972 | Dietzsch et al. | 204/301 |

FOREIGN PATENT DOCUMENTS 2118975 11/1983 United Kingdom .

*Primary Examiner*—John F. Niebling
*Assistant Examiner*—John S. Starsiak, Jr.
*Attorney, Agent, or Firm*—Charles E. Smith; James W. Williams, Jr.; James C. Bolding

[57] ABSTRACT

A method and apparatus for the continuous separation of a target protein from a protein mixture containing two or more proteins and at a pH equal to the pI of the target protein is disclosed. The method and apparatus employ a non-ionic, non-electrically conductive porous conduit through which the protein mixture is passed. The conduit is subjected to the influence of an electrical field substantially perpendicular to the flow of fluid therethrough resulting in movement of all charged protein from the conduit lumen. The target protein, which is unaffected by the electric field since it is not charged at a pH equal to its pI, is collected from the conduit outlet in substantially purified form.

5 Claims, 5 Drawing Sheets

CONTINUOUS ISOELECTRIC SEPARATION

Cross-Reference To Related Applications

This application is a continuation-in-part of Ser. No. 140,855 filed Jan. 5, 1988, now abandoned.

BACKGROUND OF THE INVENTION

1. Field of the Invention

The present invention provides a method and apparatus for continuous separation of proteins. More particularly, the invention involves the separation of proteins or protein fractions based on the difference in their isoelectric points. The method is easily carried out using an apparatus such as the hollow fiber membrane apparatus described herein.

2. Description of Related Art

A number of systems to separate proteins using electric fields have been described in the literature. These systems range from analytical devices to large scale (i.e. preparative) continuous purification systems. A number of common problems are shared by these electrophoretic systems. One problem is the convection due to heat generated by the electrolysis. Another problem is that electrophoretic systems separate all components of the input mixture making the separation more tedious, complex and expensive than necessary since usually only one component of the protein mixture is the desired product.

In analytical systems some type of anticonvective medium is typically used. For example, polyacrylamide gel, sucrose gradient or a bed of packed beads provide the anti-convective medium in many systems. The polyacrylamide gel system has the additional advantage that the gel acts not only as the convective stabilizer but also increases resolution by a sieving effect. The major limitations of these analytical systems are that they are not practical to scale up and are typically single use devices since the gels cannot be reused, typically, due to the configuration of such devices.

Some currently used means of stabilizing against convection in large scale systems are to operate under zero gravity (i.e. in earth orbit) or to produce a laminar flow field between two rotating cylinders (CTB Developments Limited, England). Amongst the major disadvantages of these systems are that they require complicated and costly devices and/or special environments to perform the separation.

SUMMARY OF THE INVENTION

The present invention is directed to a method and apparatus for the continuous separation of a target protein, from a protein mixture containing two or more proteins, at a pH substantially equal to the pI of the target protein. The method and apparatus employ a non-ionic, non-electrically conductive porous conduit along which the feed protein mixture is passed, and through which the undesired protein is passed in the course of the effected separation. To accomplish this effect the conduit is subjected to the influence of an electrical field substantially perpendicular to the flow of fluid therethrough resulting in movement of all charged protein from the conduit lumen by passage through the walls of the conduct along the lines of electric field force. The target protein, which is unaffected by the electric field since it does not have a net charge at a pH equal to its pI, is collected from the conduit outlet in substantially purified, and not excessively diluted, form.

The optimal separation can be achieved utilizing the present method and apparatus when conduit wall diffusion properties and flow rate through the conduit are such that 1) loss of the desired protein through passive diffusion is limited with respect to the rate at which said protein passes through the conduit; 2) the pressure within the conduit is maintained at a pressure lower than the pressure outside the conduit such that significant diffusive flow of the desired protein through the wall is not induced by a pressure differential across the wall; 3) the pressure within the conduit is not so great that a negative pressure differential is maintained so as to cause significant dilution of the desired protein by passage of water into the conduit from the external region due to the maintained negative pressure differential; and 4) the conduit dimensional properties are adjusted to minimize convective diffusion with respect to the passage of fluid through the conduit.

DEFINED TERMS

By "net charge" is meant the overall electrostatic charge of a molecule at a particular pH and ionic strength.

By "pI" is meant the pH at which the protein has a net charge of zero.

By "electrophoretic mobility" is meant the movement exhibited by a charged molecule under the influence of an electric field.

By "target protein" is meant the protein which is to be selectively separated from a solution comprising two or more proteins By "positive pressure differential" is meant that the pressure inside the conduit is greater than the pressure outside the conduit.

STATEMENT OF THE INVENTION

The present invention provides a method and apparatus for purifying a target protein or protein fraction from other components of a protein mixture which other components possess different net charges from the target protein or protein fraction. The difference in net charge of the various proteins depends upon the pH of the protein solution to be separated and the pI of the various proteins comprising the solution.

In one aspect the present invention provides a useful apparatus for the continuous purification and collection of a target protein or protein fraction which comprises:

a) a first buffer chamber having an inlet port and an outlet port for the ingress and egress of buffer fluid;
b) a second buffer chamber having an inlet port and an outlet port for the ingress and egress of buffer fluid;
c) at least one non-ionic, non-electrically conductive membrane conduit of substantially uniform diameter, i.e., constant flow character, having an inlet port and an outlet port for the ingress of feed protein solution to be separated and the egress of the target protein solution, said conduit positioned to serve as a septum between said buffer chambers and preferably, adapted with respect to its physical, chemical, biologically interactive, and porosity properties to permit the free flow of electrophoretically-driven proteins across the diameter of the conduit;
d) a cathode electrode contained in said first buffer chamber;
e) an anode electrode contained in said second buffer chamber; and
f) a direct current power source connected to said electrodes, said power source adapted to induce an electric field through a suitable buffer contained in said chambers and sufficient to induce an electrophoretic force on charged proteins of the protein solution to be separated, said field and electrophoretic force preferably being of sufficient uniformity to effect sufficient isoelectric resolution to separate the desired protein from other proteins in the mixture to be separated, said electrodes being adapted when connected to said power source, to induce an electric field substantially uniformly in a single direction and said membrane conduit being positioned such that the electric field is substantially uniformly perpendicular to the direction of fluid flow through the membrane conduit.

Figure 1:
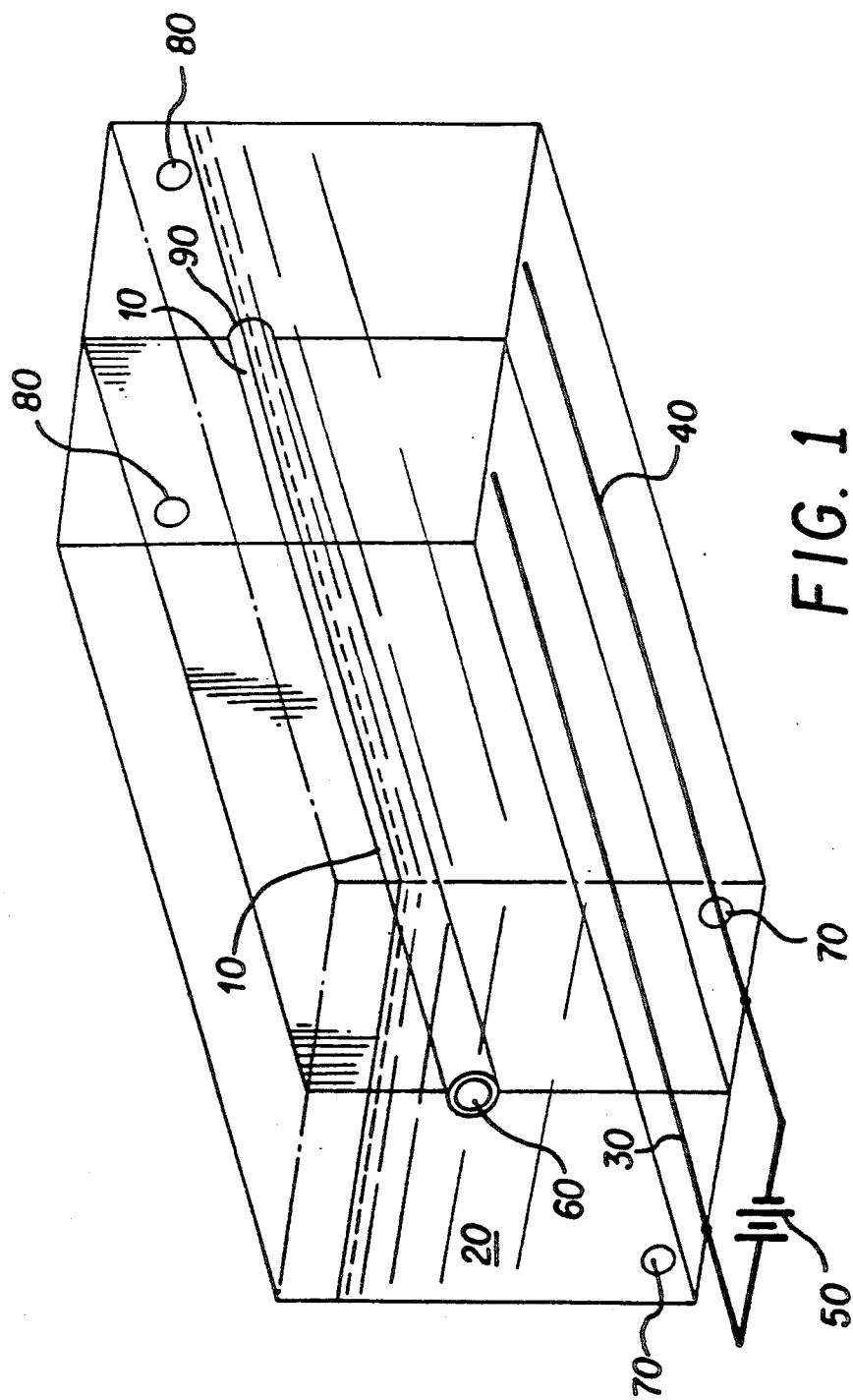
FIG. 1 represents a simple embodiment of an apparatus of the present invention useful in the isoelectric separation of proteins.

In its simplest terms, the exemplary apparatus of FIG. 1 consists of a hollow fiber membrane 10 mounted in a linear fashion such that an electric field can be applied perpendicular to the direction of fluid flow down the fiber bore. The electric field is generated substantially uniformly in a single direction by carrying out electrolysis on a solution of current carrying buffer 20 using a positive electrode (anode) 30 and a negative electrode 40 (cathode) connected to a direct current (D.C.) power source 50. The electrodes 30 and 40 are of a configuration such that the electric field induced upon the hollow fiber membrane 10 is uniformly perpendicular to the fluid flow through such membrane. Thus, where multiple conduits are utilized, similarly configured multiple electrodes, or a single plate electrode, is preferable in order to generate an electric field which is substantially perpendicular to the fluid flow through such conduit(s).

The hollow fiber membrane 10 acts as the septum of the system and, through its porosity, permits the flow of the ionic components of the buffer such that a uniform electric field gradient is established across the diameter of the fiber conduit. To this end, it is preferred that the configurations of the conduit be adapted to facilitate uniform flow therethrough, i.e., well defined flow field vector, such that convective flow patterns are reduced to the extent that there is no interference with the free flow of electrophoretically-driven proteins across the diameter of the conduit. Thus, the diameter of the inlet and outlet ports of the conduit should be of the same as or substantially similar to the diameter of the conduit membrane so that convective flow patterns are minimized.

Figure 2:
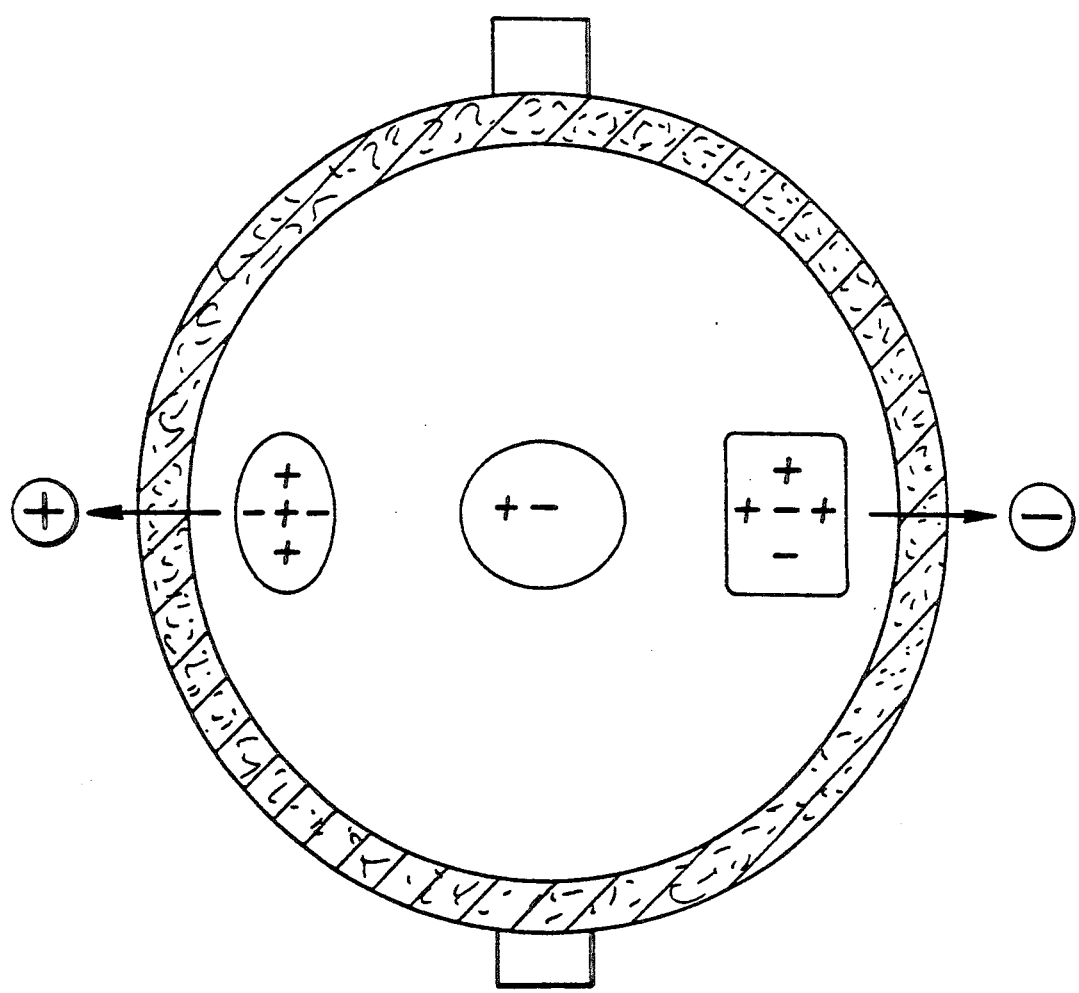
FIG. 2 represents the attractions induced upon the proteins comprising the feed material as a result of the electric field.

When a feed protein solution is pumped into the inlet of the fiber the proteins possessing a net charge are driven by the effect exerted by the electric field. As represented in FIG. 2, proteins with a net negative charge are forced in the direction of the anode. Molecules with a net positive charge are forced toward the cathode. Neglecting second order charge fluctuating effects, molecules with a net charge of zero are not effected by the electric field.

Therefore, if the pH of the inlet mixture is adjusted to the isoelectric point of the target protein, the target protein will have a net charge of zero. The contaminating proteins which possess a different isoelectric point will be affected by the electric field as described above since they will possess a net charge. The target protein will not be affected by the electric field since it will have no net charge at a pH equal to its isoelectric point. Of course, the pH of the inlet mixture can be adjusted to within about 0.1 pH units, such as within about 0.01 pH units, and effective separation can be achieved. However for optimal results, the pH of the inlet mixture should be adjusted to within about 0.001 pH units.

The fate of the contaminating proteins impinging the fiber wall is dependent on the pore size of the membrane used in the system, on the nature of the pore structure, its interactive (hydrophobic or hydrophilic) properties with respect to the protein, and by any material or modification of the pore surface or material placed within the pores. For example, if the pore size of the membrane is large enough to allow the molecule to pass there through, the molecule will exit the lumen of the fiber and enter into the wall of the membrane and eventually, given enough time, will pass through the conduit wall and exit the fiber thereby entering the adjoining buffer chamber.

It is preferable that the orientation of electric field to conduit axis be substantially perpendicular. This is an important aspect of the present invention because when an electric field is applied to the charged particles contained in the sample stream, the force which moves such particles thereby causing them to impinge on the walls of the conduit is preferably substantially perpendicular with respect to such walls. A force in another direction tends to create forces within the conduit membrane in addition to the flow and electric field forces. For example, a force in another direction (1) will force the charged particles in the direction of flow thus contaminating the collected sample stream containing the target protein and/or (2) will force the charged particles to move against the flow thereby creating convective forces which further disrupt flow separation and will reduce achievable resolution and will further contaminate the collected sample stream containing the target protein, and/or (3) will create significant convective forces by forcing charged particles to areas of the conduit membrane without causing them to impinge the conduit wall. Such convective forces significantly interfere with free flow of electrophoretically-driven proteins through the membrane thereby decreasing the capability of the apparatus to purify the target protein from the feed protein mixture.

Under circumstances wherein the contaminating proteins impinge or pass through the walls of the conduit, the separation apparatus can be operated continuously. Referring again to FIG. 1, feed material is pumped into the inlet of the hollow fiber 60. Buffer is pumped into the inlet of each buffer chamber 70 while waste buffer exits at the outlets of each buffer chamber 80 carrying away unwanted components of the feed material. The target protein is collected continuously at the outlet of the hollow fiber 90 in a substantially purified form.

Membranes which are suitable for use in the present apparatus must be non-ionic and electrically non-conductive. The selected membranes must be porous enough to permit the contaminating proteins to impinge or pass through the wall of the membrane in whatever form and with whatever modification or addition may be made to the membrane to alter its properties. Suitable membranes can be either hydrophilic or hydrophobic and can be made of polymers or ceramic material including, but not necessarily limited to, polysulfone, polyethersulfone, polypropylene, polyvinylidene difluoride, various ceramics, and the like.

While a preferred situation is to have a membrane which is porous enough to let all contaminating proteins exit into the buffer chambers in contact with the hollow fiber membrane, the membrane porosity and other properties in combination with the conditions of operation should be such that the feed mixture containing the desired protein preferably does not undergo any appreciable amount of filtration through the walls of the conduit. The filtration driving force can also transport material from the fiber bore but in a relatively nonselective fashion, hence as described above the pressure differentials across the fiber wall should preferably not be positive.

The filtration effects can be minimized by a combination of apparatus design and membrane construction. The apparatus must be designed to prevent any significant pressure drop from developing across the membrane wall. This includes any hydrostatic or dynamic pressures that may arise in the system. For example, hydrostatic pressures due to the presence of the hollow fiber membrane can be reduced by keeping the fiber minimally submerged in buffer. Also, the hydrostatic pressure at the lumen inlet and lumen outlet should be such that substantially no net flow of buffer across the membrane wall occurs.

Dynamic pressure also imposes constrains on the apparatus design because some pressure drop must exist along the length of the hollow fiber for bore flow to occur. Thus the pressure change dynes/cm², ΔP, is given by:

$$\Delta P = F \frac{8\eta l}{\pi r^4}$$

where F is the bore flow in cm³/sec, $\eta$ is the solution viscosity in gm/cm-sec, r is the radius of the hollow fiber lumen in cm and l is the length of the hollow fiber. The flow of material from the fiber lumen due to filtration effects, Q (cm³/sec), is then given by:

$$Q = L_p \times A \times \frac{P}{2}$$

where $L_p$ is the hydraulic permeability of the membrane in cm³/dyne-sec and A is the surface area of the fiber lumen in cm² (e.g. $\pi \times 2r \times l$). Hence, if the amount of material exiting the fiber due to filtration is to be less than X % of the feed material pumped into the fiber inlet the following conditions must hold:

$$X\% > \frac{Q}{F} \times 100 = L_p \frac{8\eta l^2}{r^3} \times 100$$

As can be seen from this equation, the lower the permeability of the membrane, the lower is the loss of material due to filtration. Also, increasing the fiber radius can have a dramatic effect on this parameter. However, as the fiber radius increases, convective disturbances will also increase which will decrease the performance of the system.

It is also important to note that the pressure drop P can be made such that it is either higher or lower than that of the surrounding buffer. In the case where it is higher, a loss of the material to the buffer chamber occurs. When P is lower (e.g. by drawing the solution into the conduit from a reservoir instead of pumping (pushing) it), no loss would occur, but there would be a a slight dilution. This dilution may re-contaminate the mixture, but it will be proportional to the ratio of the volume of the conduit to that of the buffer chamber, which is normally very small. Contamination will also be minimized by keeping fresh buffer chambers.

Production of a membrane with large pores to let the contaminating proteins exit the fiber lumen, but which will also present a large resistance to flow of liquid across the wall, poses a dilemma because large pore membranes typically have large hydraulic permeabilities. Therefore, one should preferably use a membrane possessing the smallest pore size that will allow the contaminating proteins to pass therethrough. However, the permeability of any chosen membrane can be further reduced without preventing proteins from being electrophoretically driven out of the fiber by a number of methods, for example, by impregnating a microporous membrane (i.e. pores greater than about 0.01 microns) with a hydrogel or other suitable resistance creating material of suitable concentration. Suitable hydrogels include, but are not necessarily limited to, agarose or polyacryamide.

Figure 7:
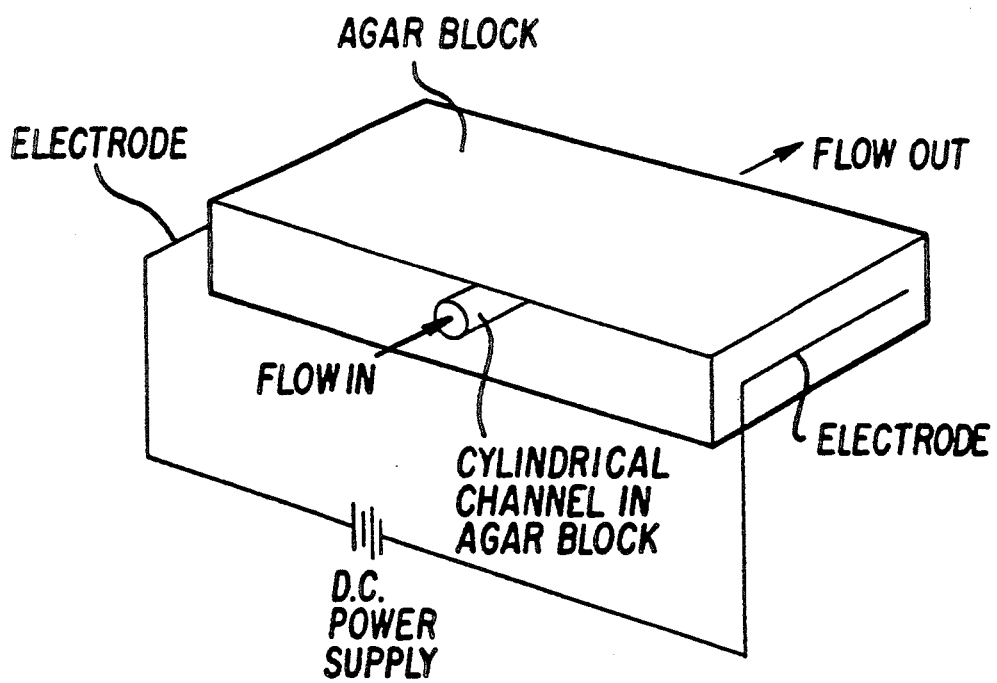
FIG. 7 represents an exemplary embodiment in which a channel formed in a slab of hydrogel serves as the conduit in place of a membrane conduit.

A hydrogel or similar such material within the pores of the membrane greatly reduces the tendency of water to move through the pores while still permitting changed proteins to pass through the membrane as they are driven by the electric field. Hence, the preferred concentration of hydrogel is the same as that used in standard protein electrophoresis separations, i.e. 0.1–1% (w/v) agarose or 1–20% (w/v) polyacrylamide. The highest concentration of hydrogel that will allow the unwanted proteins to be electrophoretically driven out of the membrane will give the greatest reduction in membrane $L_p$. If this is not sufficient, the $L_p$ can be further reduced by coating the outside of the membrane with a layer of the hydrogel. Increasing thickness of the external coating will reduce the effective $L_p$ of the membrane until the desired level is reached. Further, in cases where the mechanical strength of the membrane is not required a channel cut into a block of hydrogel can be used to carry out the separation. see FIG. 7.

In addition to losses due to filtration, one must operate the apparatus in such a manner to minimize losses due to diffusion of target protein from the fiber lumen. Reduction of diffusional losses can be accomplished by minimizing the residence time of the target protein in the fiber lumen.

The resolving capability of the apparatus is determined by its ability to separate proteins exhibiting a net charge at the pH equal to the isoelectric point of the target protein. This capability is primarily dependent on the time necessary to drive a charged protein from the fiber lumen. Therefore, if the time to clear a specific protein is given by:

$$t_c = \frac{2rf}{qE}$$

where
f = friction coefficient
q = protein charge
E = electric field strength
r = fiber lumen radius
and the residence time for the protein in the fiber bore is given by:

$$t_r = \frac{\pi r^2 l}{F}$$

then the resolving capability will be maximized when $t_c = t_r$. It therefore holds that the smallest charge qmin that can be separated is given by:

$$qmin = \frac{2Ff}{\pi rlE}$$

The apparatus and methods of the present invention are useful in the recovery of product protein from a production process. Alteratively, one can employ an apparatus of the present invention to monitor a production process by diverting a small slip stream of a process. The sip stream is the feed stream to the apparatus following any necessary preparation (i.e. pH adjustment).

The fiber bore outlet of the apparatus may be directly linked to a spectrophotometer to continuously monitor the level of target protein in the process stream from which the slip stream is obtained.

The optimum apparatus will include a membrane conduit having a radius such that $t_c$ is minimized, to yield results in a reasonable period of time, without increasing convection due to flow and/or heat. For example, referring to the formulas above, for $t_c$ to be equal to $t_r$ the following relationship for E holds:

$$E = F/\pi rql$$

Therefore as r is increased, must be increased (where the other parameters have been adjusted for optimal resolution). As stated above such increase in E increases convective forces due to heat. The radius of the membrane conduit will range between about 0.05 and about 0.60 centimeter, such as between about 0.075 centimeter and about 0.45 centimeter, preferably between about 0.15 and 0.30 centimeter. Thus, where large quantities of target proteins are desired, it may be necessary to utilize multiple conduit membranes in order to maintain optimum separating properties while handling higher throughputs.

Figure 4:
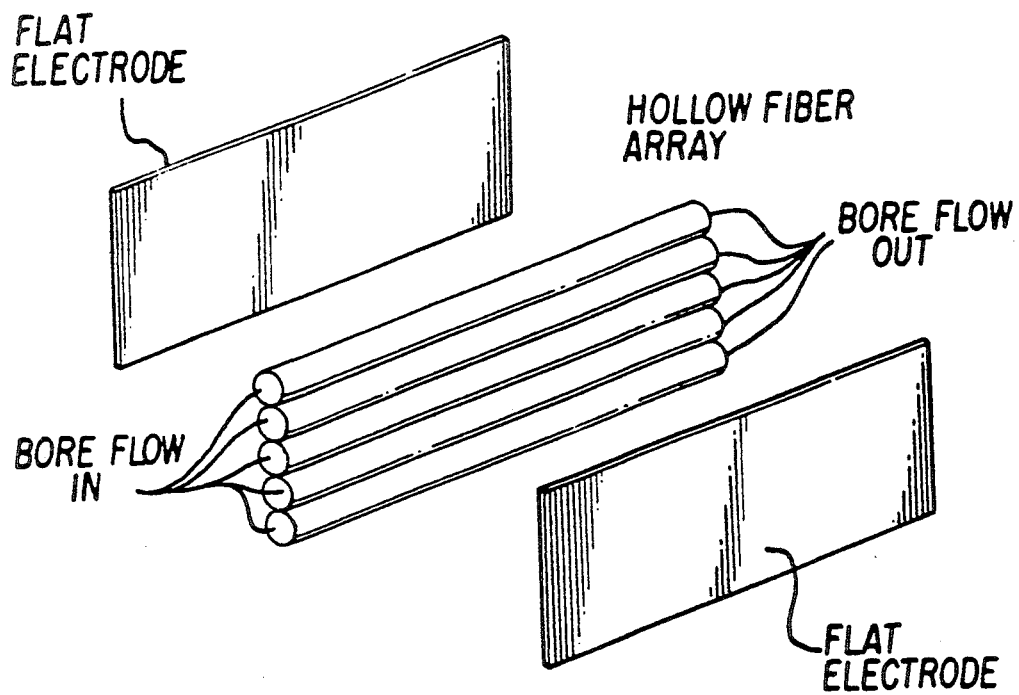
FIG. 4 represents an exemplary embodiment of the present invention comprising a plurality of hollow fiber membrane conduits.
Figure 5:
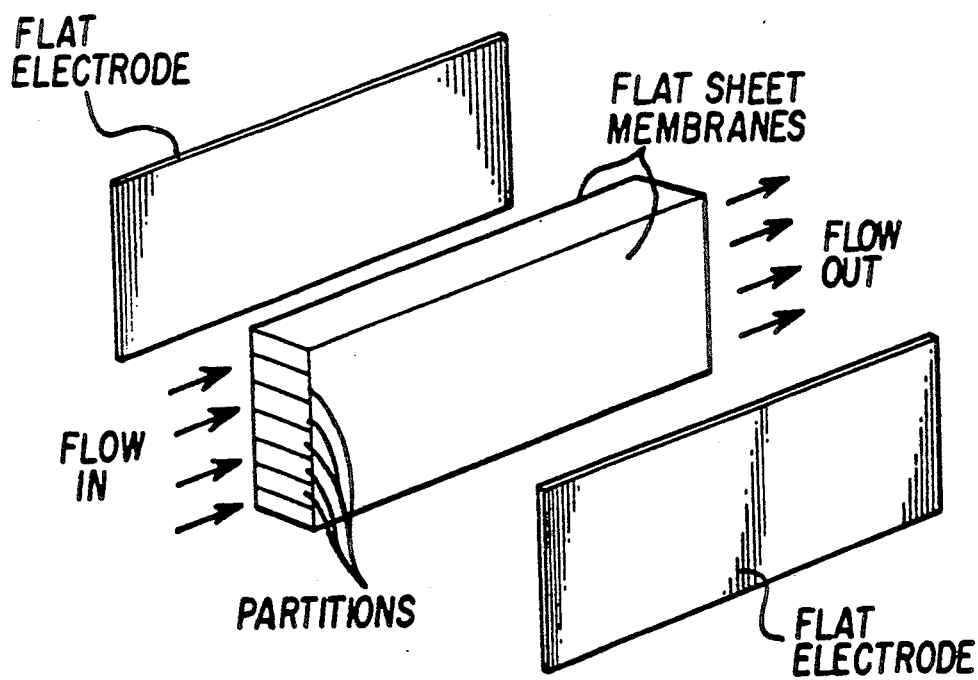
FIG. 5 represents an exemplary embodiment of the present invention comprising a multi-conduit membrane system made from flat sheet membranes.
Figure 6:
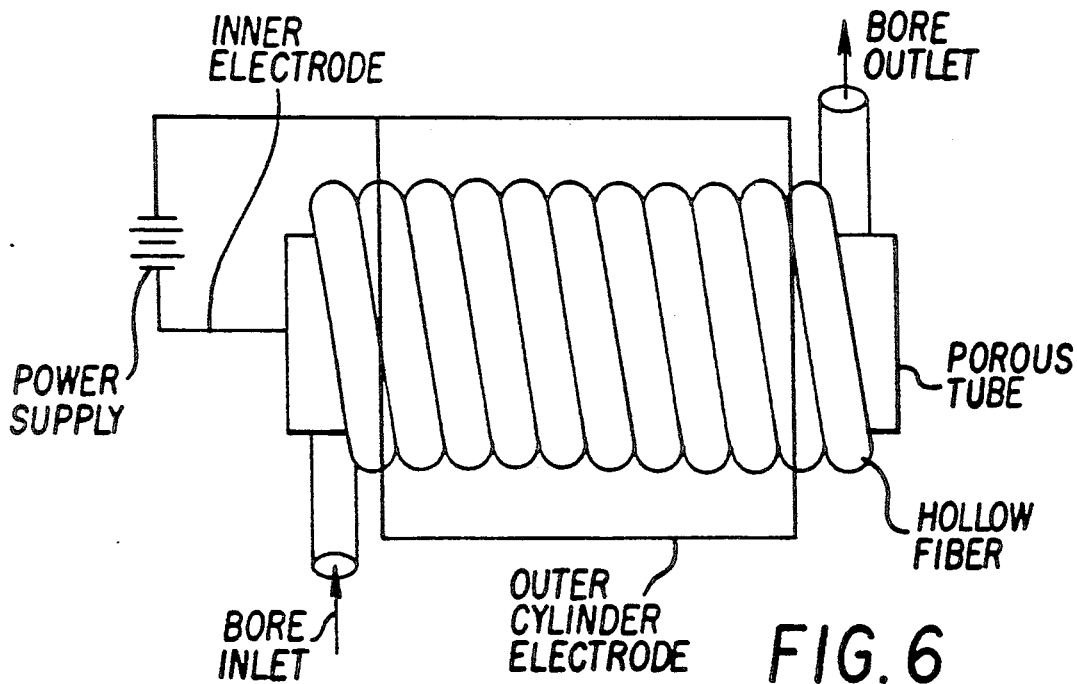
FIG. 6 represents an exemplary embodiment of the present invention comprising a spiral wound hollow fiber membrane.

FIGS. 4 through 6 illustrate several alternative embodiments of the present invention. In cases where the instant apparatus is employed as a primary means of protein product recovery a plurality of fibers will most often be used. FIG. 4 represents a multiple membrane conduit apparatus in which a plurality of hollow-fibers are used. FIG. 5 represents a multiple membrane conduit apparatus in which a channel defined by two flat sheet membranes is divided into a plurality of membrane conduits by fabricating numerous septums between the two flat sheets.

The length of the apparatus may be reduced by using other configurations for the individual fibers. For example, FIG. 6 represents a spiral wound hollow fiber apparatus in which one electrode is contained in the center of the coil and the other electrode surrounds the coil and is in the form of a cylinder. Alteratively, the fiber length of the apparatus of FIG. 1 may be increased by having the fiber fold-back on itself to make multiple passes while still being positioned in the plane separating the two buffer chambers. In a particularly preferred embodiment, an apparatus of the present invention will be constructed such that the electric field strength is at least about 1 volt/centimeter (v/cm), such as at least about 10 v/cm, preferably at least about 5 v/cm. The ratio of fluid flow per conduit to electric field strength is then between about 0.001 square centimeter per volt second ($cm^2$/vs) and about 2 $cm^2$/vs, such as about 0.01 $cm^2$/vs and about 1.5 $cm^2$/vs, preferable, between about 0.1 $cm^2$/vs and about 1.0 $cm^2$/vs.

The following examples are provided to more fully elucidate the practice of the present invention and are in no way intended to limit the scope of the invention.

EXAMPLE 1

A 0.2 micron pore size polypropylene fiber membrane was impregnated with 1% (w/v) agarose in the manner. The dry hydrophobic membrane is wetted by submerging it in isopropanol at room temperature for at least 15 minutes. The alcohol is exchanged for water by exhaustive washing of the wetted membrane. The re-wetted polypropylene membrane is then submerged in a 1% agarose solution maintained at about 60° C. for about 16-24 hours. The membrane is then removed from the agarose solution and drained of excess hydrogel. Upon cooling the agarose solidifies and the membrane is ready to use. The membrane was mounted in the chamber shown in FIG. 1.

The carrier buffer was 0.06 molar barbital buffer pH 8.6. A mixture of proteins, cytochrome C, phycocyanin and gamma globulins dissolved in babital buffer, was pumped into the lumen of the hollow fiber membrane. An electric field was applied to the system such that 40 mA of current was generated. The negatively charged phycocyanin migrated toward the positive electrode, the positively charged cytochrome C migrated toward the negative electrode and the gamma globulins remained substantially inside the hollow fiber membrane. The red colored cytochrome C and the blue colored phycocyanin could be seen exiting the hollow fiber membrane into surrounding buffer chambers. The presence of gamma globulins inside the membrane and the selective removal of cytochrome C and phycocyanin was confirmed by gel electrophoresis analysis.

EXAMPLE 2

Figure 3:
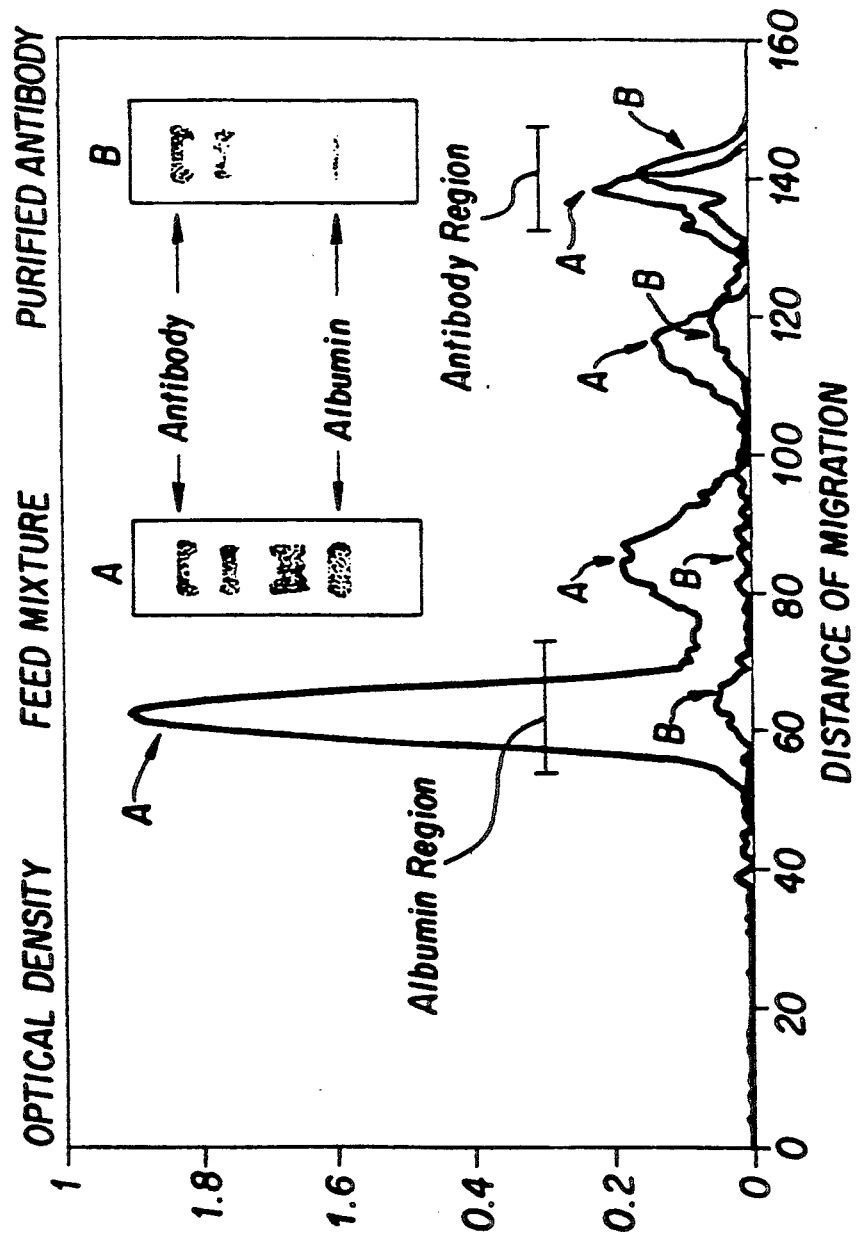
FIG. 3 illustrates an optical density of the electrophoresis gel of the purified material of Example 2 versus the crude feed material.

A mixture of 1.25 mg/ml IgG2b, kappa monoclonal antibody from lyophilized mouse ascites plus 20% fetal bovine serum in del Becicos medium was dialyzed against 0.2M phosphate buffer, pH 7.0. The mixture was pumped into the hollow fiber membrane (1.8 ml per 64.3 minutes) apparatus described in Example 1. The buffer chambers contained 0.175M phosphate buffer pH 7.0, a voltage of 22V and a current of 1A was generated in the system. The material flowing out the outlet of the fiber lumen was analyzed by gel electrophoresis. Referring to FIG. 3, the data show that a substantial enrichment of antibody in the product solution was achieved.

Those skilled in the art will recognize that various modifications and equivalents of the present invention may be made and employed without departing from the spirit and scope of the present discovery. Hence, such equivalents are to be considered within the scope of the appended claims.

I claim:

1. An apparatus for continuous purification and collection of a target protein or protein fraction which comprises:
    a) a first buffer chamber having an inlet port and an outlet port for the ingress and egress of buffer fluid;
    b) a second buffer chamber having an inlet port and an outlet port for the ingress and egress of buffer fluid;
    c) at least one nonionic, nonelectrically conductive porous membrane conduit of substantially uniform diameter and of constant flow character having an inlet port and an outlet port for the ingress of feed protein solution to be separated and the egress of the target protein solution, said conduit having an inside diameter and an outside diameter and said inlet and outlet ports having an inside diameter which is substantially the same as the inside diameter of the conduit, said conduit being positioned to serve as a septum between said buffer chambers and adapted to permit the free flow of electrophoretically-driven proteins therethrough;
    d) a cathode electrode contained in said first buffer chamber;
    e) an anode electrode contained in said second buffer chamber; and
    f) a direct current power source connected to said electrodes, said power source adapted to induce an electric field through a suitable buffer contained in said chambers and sufficient to induce an electrophoretic force on charged proteins of the protein solution to be separated;

said electrodes being adapted, when connected to said power source, to induce an electric field substantially uniformly in a single direction, and said membrane conduit being positioned such that the electric field induced by said power source is uniformly substantially perpendicular to the direction of fluid flow through the membrane conduit.

2. An apparatus of claim 1 in which the membrane conduit is made of a polymer selected from the group consisting of polysulfone, polyethersulfone, polypropylene and polyvinylidene diflouride.

3. An apparatus of claim 1 in which the membrane conduit is impregnated with a hydrogel to decrease its hydraulic permeability.

4. An apparatus of claim 3 in which the membrane conduit is impregnated with a hydrogel selected from the group consisting of agarose and polyacrylamide.

5. An apparatus of claim 2 in which the membrane conduit is made of polysulfone.

* * * * *